United States Patent [19]

Perry

[11] 4,341,220

[45] Jul. 27, 1982

[54] STEREOTACTIC SURGERY APPARATUS AND METHOD

[75] Inventor: John H. Perry, Silver Spring, Md.

[73] Assignee: Pfizer Inc., New York, N.Y.

[21] Appl. No.: 29,865

[22] Filed: Apr. 13, 1979

[51] Int. Cl.³ .......................................... A61B 17/00
[52] U.S. Cl. ............................... 128/630; 128/303 B
[58] Field of Search .................. 128/303 B, 630, 653, 128/659, 660; 250/312, 445 T, 491, 476; 269/322; 33/174 D, 174 J

[56] References Cited

U.S. PATENT DOCUMENTS

| | | | |
|---|---|---|---|
| 3,508,552 | 4/1970 | Hainault | 128/303 B |
| 3,714,428 | 1/1973 | Gasaway | 250/312 |
| 3,867,634 | 2/1975 | Hounsfield | 250/445 T |
| 4,005,527 | 2/1977 | Wilson | 33/111 |
| 4,071,769 | 1/1978 | Brunnett et al. | 250/445 T |
| 4,115,691 | 9/1978 | Oldendorf | 250/312 |
| 4,174,481 | 11/1979 | Liebetruth | 250/445 T |
| 4,197,855 | 4/1980 | Lewin | 128/653 |
| 4,228,799 | 10/1980 | Anichkov | 128/303 B |

FOREIGN PATENT DOCUMENTS

| | | | |
|---|---|---|---|
| 1206116 | 12/1965 | Fed. Rep. of Germany | 128/303 B |
| 107206 | 8/1963 | Netherlands | 128/303 B |
| 7506593 | 12/1975 | Netherlands | 128/659 |
| 818711 | 8/1959 | United Kingdom | 128/303 B |
| 202452 | 9/1967 | U.S.S.R. | 128/303 B |

Primary Examiner—Robert W. Michell
Assistant Examiner—J. L. Kruter
Attorney, Agent, or Firm—Cushman, Darby & Cushman

[57] ABSTRACT

X-ray detectable fiducial markers are associated with a stereotactic surgery frame. The frame is fixed with respect to a patient's anatomy and defines a predetermined three-dimensional coordinate system in which surgical devices may be precisely positioned. A desired target area of the anatomy is detected in a cross-sectional CT scanner depiction of the combined stereotactic frame and patient anatomy. The target's coordinates with respect to the frame are calculated based on three non-collinear fiducial points also located within the cross-section and having known coordinates both with respect to the frame and with respect to the target.

In the exemplary embodiment, detachable fiducial point-defining members are associated with a stereotactic surgical frame. For example, each member may be a plate having a series of parallel grooves or slots which progressively increase in length from one slot to the next. The frame coordinates of the end points of each slot are predetermined and known. Thus three fiducial points with respect to the frame can be determined by simply counting the number of slots or grooves contained within the cross-sectional depiction and thereby determining which end point is within such cross-section.

31 Claims, 8 Drawing Figures

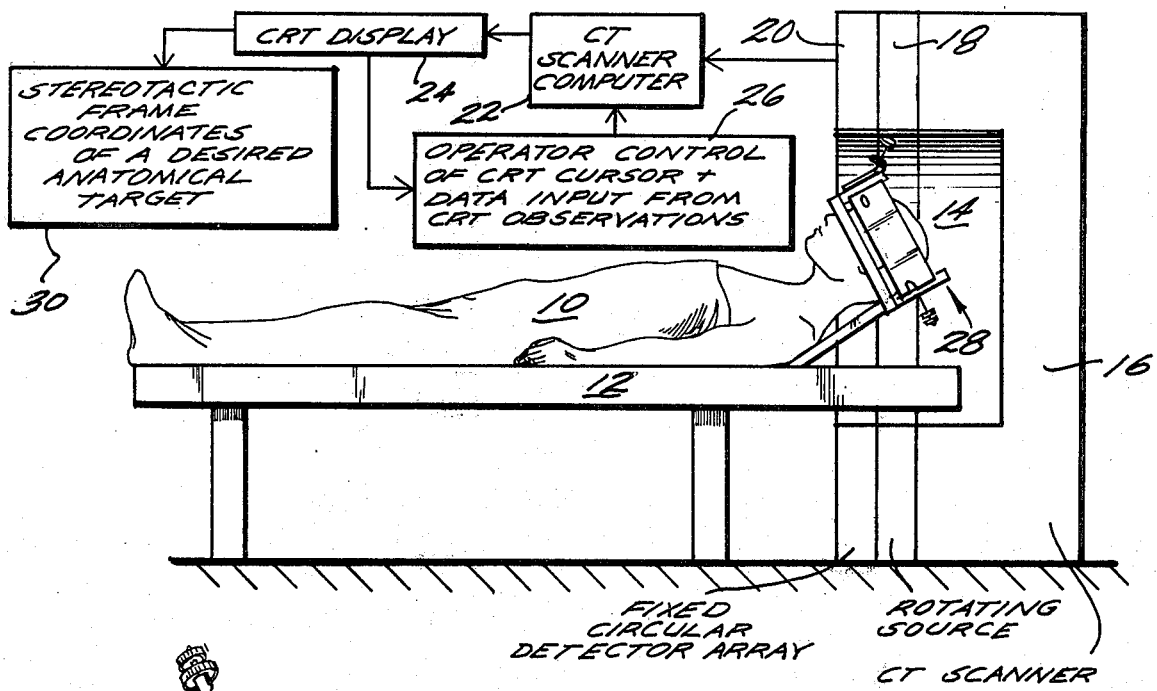
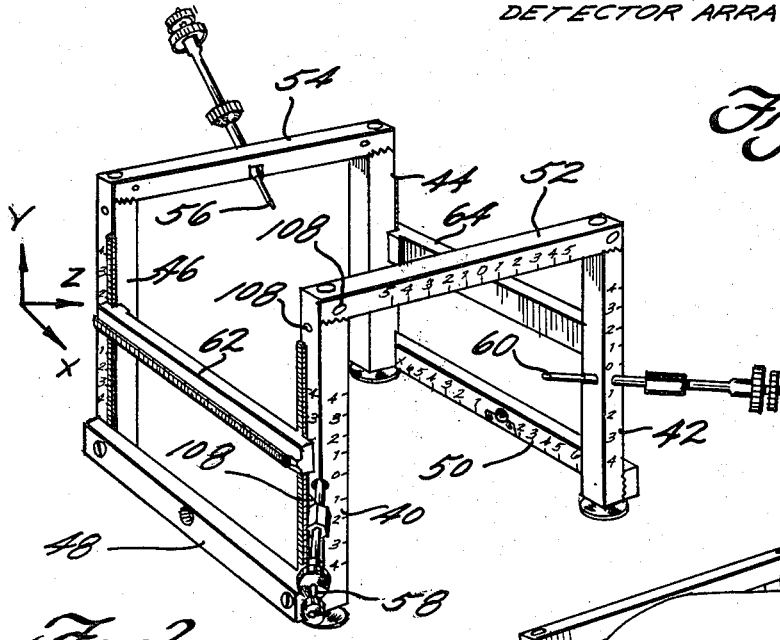
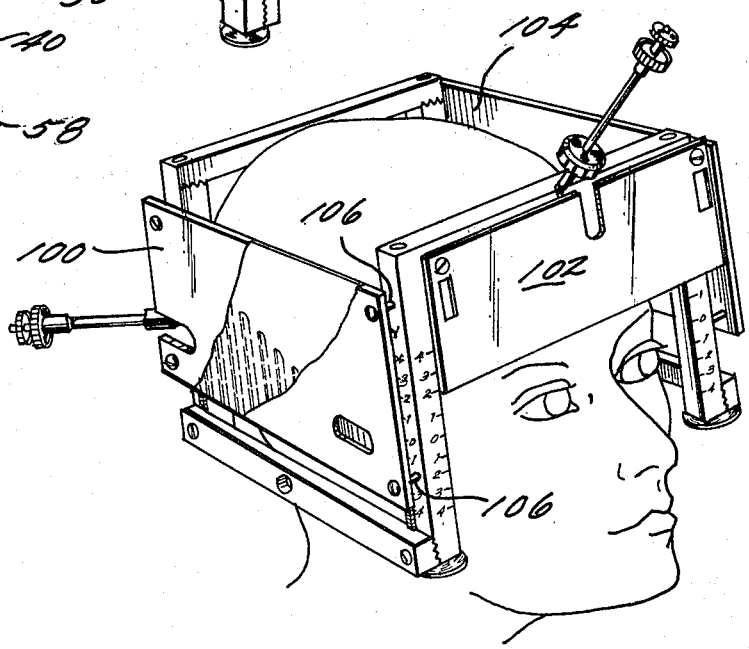
Fig. 1
Fig. 2
Fig. 4

STEREOTACTIC SURGERY APPARATUS AND METHOD

This invention generally relates to stereotactic surgical apparatus and method. In particular, the invention pertains to method and apparatus which permits more accurate use of stereotactic frames than has heretofore been possible.

In the past, stereotactic surgery has been somewhat of an art based upon average or other statistical measurements of anatomical structures. Thus, although many varied surgical devices can be precisely positioned within a predetermined three-dimensional coordinate system defined by the stereotactic frame, there were no precision procedures for determining the exact location of a specific anatomical location or target area of a specific patient within such a coordinate system.

Since computed tomographic (CT) X-ray scanners have come into common usage, attempts have been made by others to utilize in stereotactic surgery the additional, more precise information available in cross-sectional depictions of anatomy provided by CT scanners. However, it is believed that these attempts by others have involved the use of data derived from multiple cross-sectional depictions taken at successive increments. The use of data taken from such plural cross-sectional depictions not only increases the necessary X-ray exposure suffered by the patient but also necessarily introduces additional errors in the resulting procedure caused by such factors as patient movement between scans, imprecise bed movements, etc.

It has now been discovered that, by suitably modifying the stereotactic frame, data required for calculating the stereotactic frame coordinates of an anatomical target can be obtained from only a single CT scan of the combined stereotactic frame and patient anatomy. In brief, the stereotactic frame is modified so as to define three fiducial points located within any such cross-sectional depiction. Coordinates are readily determinable or are known for these fiducial points with respect to both the stereotactic frame and with respect to the CT scanner. Since the desired anatomical target area also has known or readily determinable coordinates with respect to the CT scanner, a relatively simple mathematical calculation may then be made to transform the target's CT scanner coordinates into corresponding stereotactic frame coordinates which may then be used during a stereotactic surgical procedure.

In the preferred exemplary embodiment, the three fiducial points within any given cross-sectional depiction are defined by three respectively corresponding fiducial plates or diagonal rods detachably mounted on three sides of the stereotactic frame. Each plate has a variable cross-section extending along a first dimension for a predetermined distance with varies with respect to a second dimension, inclined with respect to said first dimension. For example, the plate may comprise a series of parallel grooves or slots having lengths which progressively increase from one slot to the next. The frame coordinates of each slot end-point are known and one can determine which end-point lies within the depicted cross-section by simply counting the number of displayed slots.

The stereotactic surgery frame may be modified in other ways to define the necessary three non-collinear fiducial points contained within a single cross-sectional depiction and having known or readily determinable coordinates both with respect to the frame and with respect to another reference system in which the desired anatomical target also has konwn or readily determinable coordinates. Once those common coordinates are known, the coordinates of the target with respect to the frame may be simply computed.

For example, another simple embodiment comprises a rod connected diagonally between spaced vertical frame members. The relative location of the rod and vertical members as intersected by any given cross-section then provide the necessary geometrical information from which the frame coordinates of the fiducial points (defined by the intersection of the rod with the depicted cross-section) can be calculated. Similarly, diagonal slots, grooves or other X-ray detectable structures can be used to define the required fiducial points in any given cross-section having known frame coordinates.

These as well as other objects and advantages of the invention will be better understood by reading the following detailed description of the presently preferred exemplary embodiment taken in conjunction with the accompanying drawings, of which:

FIG. 1 is a diagrammatic and block diagram description of an improved stereotactic surgical head frame according to this invention in use with a conventional X-ray CT scanner to facilitate a stereotactic surgical procedure;

FIG. 2 is a perspective view of a conventional stereotactic surgical frame except for mounting holes provided to receive special fiducial plates;

FIG. 4 is a perspective view of the modified stereotactic frame shown in FIG. 3 after fixation to the living anatomy of a patient;

Figure 3:
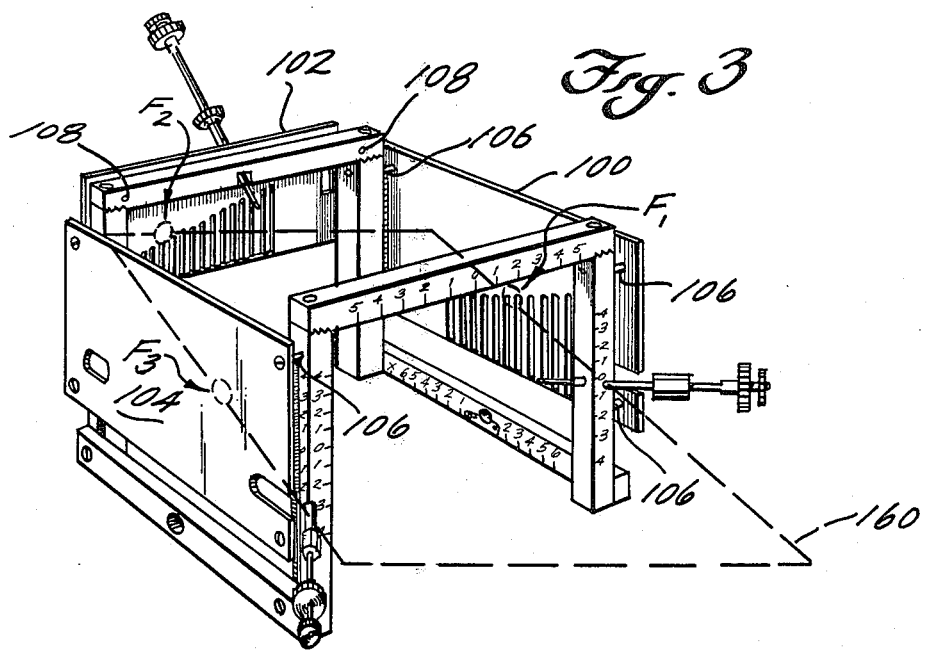
FIG. 3 is a similar perspective view of the frame shown in FIG. 2 but with three fiducial marker plates attached in accordance with this invention.

Referring to FIG. 1, a patient 10 is placed on a bed 12 and moved into the patient circle 14 of a CT scanner 16. There are many CT scanners presently available on the market and the showing in FIG. 1 is a diagrammatic depiction of a so-called fourth generation scanner having a rotating X-ray fan beam source 18 operating in conjunction with a fixed circular array of detectors 20 to provide the necessary radiation absorption data from a multiplicity of angles through a desired portion of the patient's anatomy. These absorption meaurements are then conventionally processed by a CT scanner computer 22 to provide a CRT display 24 depicting the density of elemental volumes within a cross-sectional "slice" of the patient's anatomy located within the patient circle 14. Other types of non-destructive penetrating radiation scanning techniques might also be used to provide the cross-sectional depiction of such internal anatomical structure (e.g. nuclear magnetic resonance).

The X-ray CT scanners presently on the market typically include an operator controlled console 26 from which the operator can control the position of a cursor on the CRT display. Based on the relative location or of tilting bed 12 (or of the scanning gantry relative to the bed) and of the cursor within any displayed "slice", the computer 22 is normally also programmed to provide, at the operator's request, the three-dimensional coordinates of any desired portion of the cross-sectional depiction relative to the geometry of the CT scanner 16.

In accordance with this invention, a modified stereotactic frame 28 is fixed with respect to a desired portion of the patient's anatomy within the patient circle 14. Thereafter, once an operator has obtained a cross-sectional depiction of the combined stereotactic frame 28 and included anatomy which also includes the desired anatomical target area for a surgical device, the operator can precisely determine the target coordinates with respect to the stereotactic frame 28.

In particular, three non-collinear fiducial points having readily determinable coordinates with respect to the frame are also depicted in the CRT display thus enabling the operator to obtain coordinates for these same fiducial points with respect to the CT scanner. Since the coordinates of the desired anatomical target area can also be obtained with respect to the CT scanner, those coordinates can easily be transformed into corresponding stereotactic frame coordinates. The mathematical transformation may be performed in another properly programmed computer or in the CT scanner computer 22 as controlled by operator inputs via the control console 26. Of course, these calculations could also be performed manually or semi-automatically (.e.g, with hand calculators or the like) if desired. If the CT scanner computer 22 has been programmed to perform the transformation, the stereotactic frame coordinates 30 of a desired anatomical target may be directly obtained from the CRT display 24.

Figure 6:
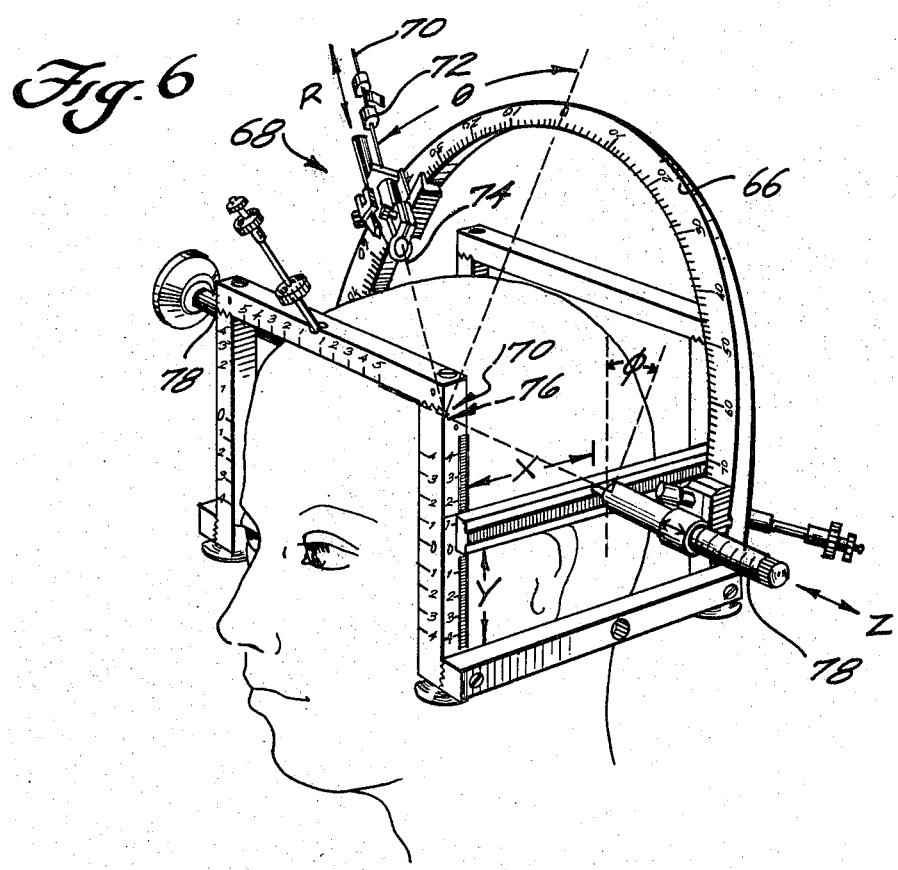
FIG. 6 is a perspective view of the conventional stereotactic surgical frame with its attched surgical device holder as it is used during surgery after removal of the fiducial marker plates shown in FIGS. 3 and 4.

The stereotactic surgical head frame shown in FIGS. 2 and 6 is, per se, well known in the prior art. One such head frame is known as a "Lexell" type of frame and another is known as the "Trentwell" type of frame. As shown in FIGS. 2 and 6, the frame includes four vertical posts 40, 42, 44 and 46 rigidly interconnected by horizontal posts 48, 50, 52 and 54. Three skull anchors 56, 58 and 60 are also provided so as to rigidly fix the stereotactic frame with respect to a human skull.

Although stereotactic surgery has normally been performed inside the skull, this invention would be equally useful with stereotactic frames and surgical procedures adapted to other portions of living anatomy as well.

Side bars 62 and 64 are adjustably attachable to the vertical posts 40–46 as shown in FIG. 2. A carrier 66 is also adjustably attached to the side bars 62 and 64 (as shown in FIG. 6) for mounting a probe carrier 68. The probe typically comprises a thin rigid cannula 70 through which or on which a surgical device is inserted on a rod-shaped holder into the brain through an opening in the skull. Any desired surgical device can be provided at the end of the probe for insertion into the brain.

Normally, a probe stop 72 is arranged so that the probe's motion along the R axis shown in FIG. 6 can be accurately controlled to place the end of the probe 74 at the center 76 of a spherical coordinate system defined by the stereotactic frame. The vertical Y dimension and the front-to-back X dimension of the origin 76 is determined by the adjustable placement of the side bars 62 and 64 and probe carrier 66 with respect to indicia carried on these various frame members. The side-to-side Z dimension of the origin 76 is determined by sliding the arcuate portion of the probe-carrier with respect to the shafts 78. Thereafter, so long as the probe end 74 is inserted to the center 76 of the thus defined spherical coordinate system, the other spherical coordinates $\theta$ and $\phi$ (see FIG. 6) are immaterial except insofar as the surgeon may choose these angles to minimize damage when the probe is inserted through other portions of the brain and/or to facilitate access to the desired portion of the brain as is common practice in stereotactic surgery techniques.

As should now be appreciated, the exemplary stereotactic frame defines both rectilinear X, Y, Z and spherical R, $\theta$, $\phi$ three-dimensional coordinate systems. Once the frame X, Y, Z coordinates of a target anatomy are determined, the frame is adjusted in X, Y, Z coordinates so as to place the target at the origin of the R, $\theta$, $\phi$ system.

Referring now to FIGS. 3 and 4, the modified frame in the illustrated exemplary embodiment includes three fiducial plates 100, 102 and 104. These frames are removably attached to the vertical frame posts through mounting pins 106 and mating, precision friction fit, apertures 108.

Figure 8:
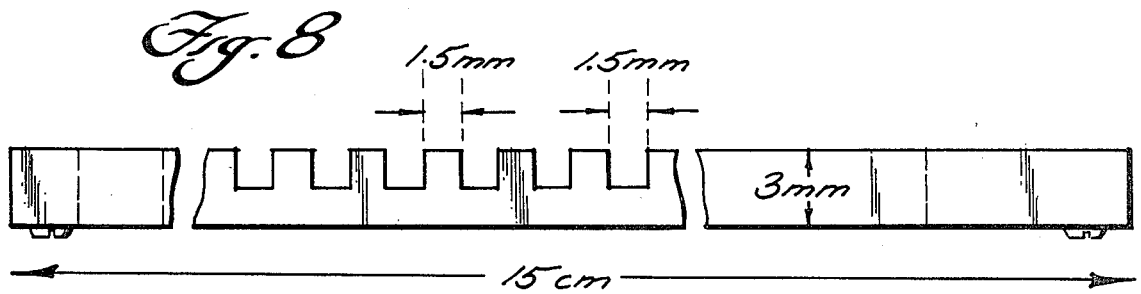
FIG. 8 is a detailed edge view of the exemplary fiducial marker plate shown in FIG. 7.
Figure 7:
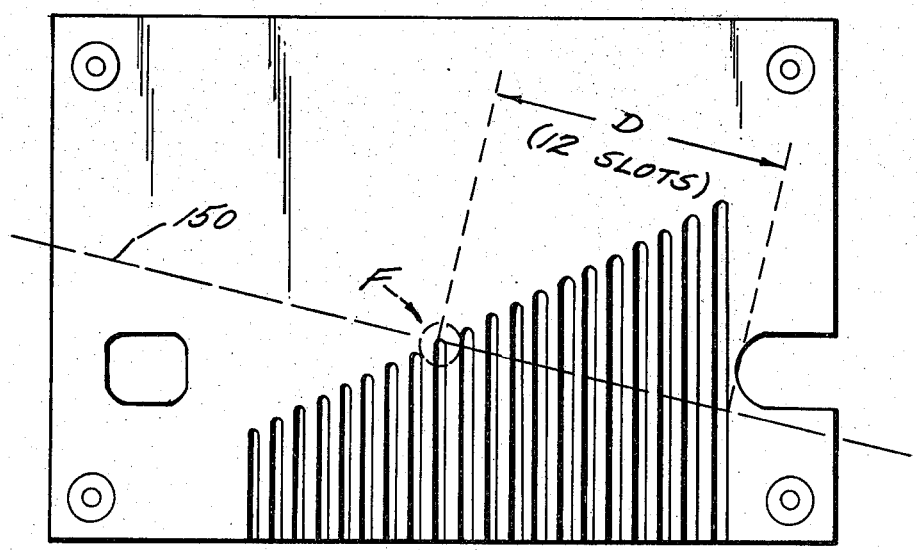
FIG. 7 is a detailed view of one of the exemplary fiducial marker plates shown in FIGS. 3 and 4.

In the exemplary embodiment, each fiducial plate has a variable cross-section along a first dimension for a predetermined distance which predetermined distance also varies in a second dimension, inclined with respect to the first dimension. For example, as illustrated in FIGS. 7 and 8, each fiducial plate includes a series of parallel grooves or slots having different respective lengths. The grooves or slots are preferably spaced regularly and of substantially equal dimensions having respective lengths which progressively increase (or decrease depending upon the direction of progression) from one slot to the next. In the exemplary embodiment the fuducial plates are constructed from aluminum.

If a cross-sectional "slice" is taken along a line 150 (FIG. 7) which intersects this pattern of variable cross-section, then the variations will be observable in any depiction of that "slice". Since the plate is fixed with respect to the frame and since the slot end points have known X, Y, Z locations with respect to the frame, a fiducial area or point F with respect to the frame will be defined by the end point included within the cross-section. This particular end point can, in turn, be determined by simply counting the number of slots included in the distance D of variable cross-section within slice 150. Preferably, slice 150 intersects the fiducial plate at least one slot from each end (e.g., more than one and less than the total number of slots would then be seen in the cross-sectional depiction).

Figure 5:
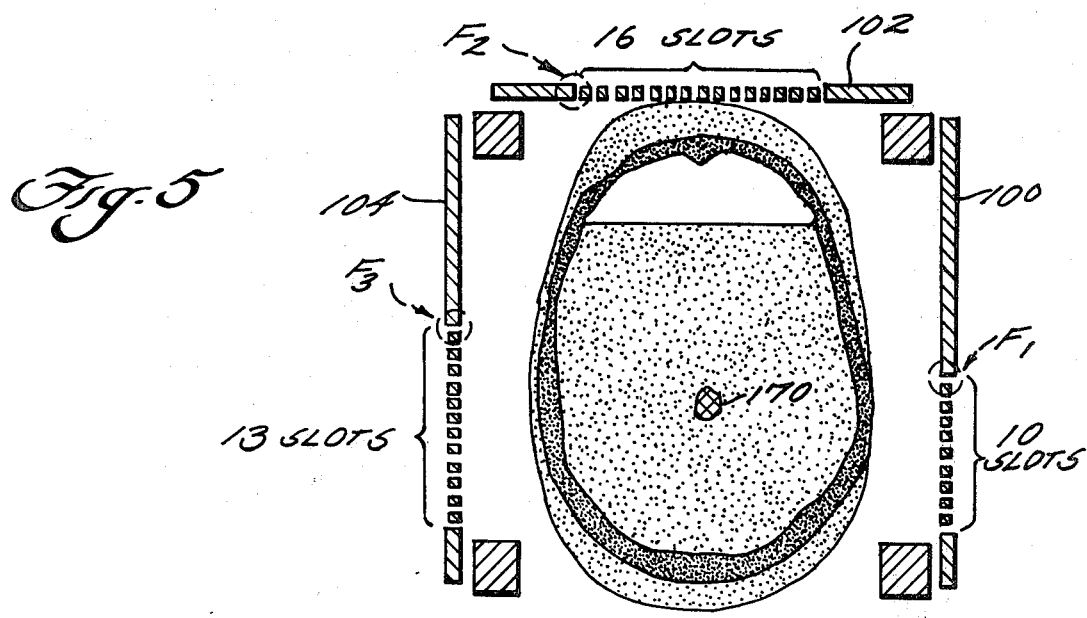
FIG. 5 is a diagrammatic representation of a cross-sectional depiction (e.g., a CT scan "slice") through the combined modified frame and anatomy shown in FIG. 4.

As schematically indicated in FIG. 3, a "slice" 160 will intersect the variable cross-sectional portions of each fiducial plate 100, 102 and 104. A typical CT scan depiction of such a slice through the combined frame and human head is shown in FIG. 5. As indicated in FIG. 5, by merely counting the number of slots included in the cross-sectional "slice" for each fiducial plate, the operator can locate three non-collinear fiducial points $F_1$, $F_2$, and $F_3$ within the slice which have known, readily determinable coordinates with respect to the stereotactic frame. At the same time, and using the same CT scan "slice", the operator can position the cursor and locate the same fiducial points with respect to a desired anatomical target area 170. Normally, the coordinates for this common three-dimensional coordinate system would be with respect to the CT scan apparatus.

Once this data has been determined, the CT scan computer 22 may be programmed to compute the frame coordinates of the target 170 which can then be used in standard stereotactic surgical procedures. If desired, the data required for this coordinate transformation calculation can be input from the operator keyboard or, alternatively, the CT scanner computer may be programmed to accept the input coordinate data corresponding to the location of a cursor at the time a special function key or the like is operated at the console 26. In this way, the operator would be relieved from the necessity of transcribing the coordinate input data onto the keyboard of the console 26 thus eliminating another source of potential error.

With presently available CT scanners, the elemental scan resolution may cause errors of more than one millimeter. Accordingly, the operator should take care to accurately locate the fudicial points $F_1$, $F_2$, and $F_3$ and to obtain their CT scan coordinates. Furthermore, the "slice" thickness may substantially contribute to errors unless care is taken by the operator to center the target 170 within the thickness of such a "slice". Similarly, care should be taken to obtain the coordinates of the target 170 with respect to the center of the target area shown on the cross-sectional depiction of the slice.

Many other types of X-ray detectable fiducial marking systems may be associated with a stereotactic frame. For example, a simple cylindrical (or any other cross-sectionally shaped) rod diagonally connected between the dissimilar portions of spaced apart pairs of posts could be used to identify three non-collinear fiducial points within any given cross-sectional slice. The relative locations of the cross-section taken through the diagonal rods with respect to the cross-sections taken through the connected pairs of posts could be used to provide the required frame coordinates of these fiducial points through simple geometrical calculations. Of course a diagonal slot or void in a plate, etc., could be similarly employed as could many other types of frame modifications.

By deriving all of the required transformation input data from only one CT scan slice, possible errors are minimized and hence this mode of the invention is preferred.

The fiducial plates in the illustrated embodiment are designed so that the frame coordinates (X, Y, Z) of the end of each slot are known. By counting the number of slots observed in a given CT slice for a given plate, one can determine which of the various slot ends are located within the plane of the displayed slice. These slot ends then constitute the three noncollinear fiducial points $F_1$, $F_2$, and $F_3$ as noted in FIG. 5. Since the X, Y, Z frame coordinates of each slot end are known, once the fiducial points have been thus identified, their frame coordinates are known.

Since the coordinates of the fiducial points $F_1$, $F_2$, and $F_3$ as well as the target area 170 can all be determined with respect to another common coordinate system, it follows that a relatively simply mathematical coordinate transformation may thereafter be used to calculate the X, Y, Z frame coordinates of the target 170.

There are several possible ways to perform the required transformation calculation. However, one straightforward approach will now be explained. For example, let capital letters denote frame X, Y, Z coordinates and lower case letters denote CT scan coordinates (or any other coordinate system for which coordinates of all of the fiducials and the target area can be measured). Using this nomenclature:

| | |
|---|---|
| $\vec{F}_1, \vec{f}_1$ = fiducial 1 | (equation 1) |
| $\vec{F}_2, \vec{f}_2$ = fiducial 2 | (equation 2) |
| $\vec{F}_3, \vec{f}_3$ = fiducial 3 | (equation 3) |
| $\vec{T}, \vec{t}$ = target | (equation 4) |

Define $\vec{A}, \vec{B}, \vec{C}, \vec{a}, \vec{b}, \vec{c}$:

| | | |
|---|---|---|
| $\vec{A} = \vec{F}_2 - \vec{F}_1$; | $\vec{a} = \vec{f}_3 - \vec{f}_1$ | (equations 5, 6) |
| $\vec{B} = \vec{F}_3 - \vec{F}_1$; | $\vec{b} = \vec{f}_3 - \vec{f}_1$ | (equations 7, 8) |
| $\vec{C} = \vec{T} - \vec{F}_1$; | $\vec{c} = \vec{t} - \vec{f}_1$ | (equations 9, 10) |

The problem is to find $\vec{T}$, the target frame coordinates.

Since $\vec{a}$, $\vec{b}$, and $\vec{c}$ lie in the same plane and a and b are not collinear, by solution of the simultaneous equations, constants $\alpha$ and $\beta$ can be found such that:

$$\vec{c} = \vec{t} - \vec{f}_1 = \alpha\vec{a} + \beta\vec{b} \quad \text{(equation 11)}$$

The equivalent in frame coordinates is:

$$\vec{C} = \vec{T} - \vec{F}_1 = \alpha\vec{A} + \beta\vec{B} \quad \text{(equation 12)}$$

Thus:

$$\vec{T} = \vec{F}_1 + \alpha\vec{A} + \beta\vec{B} \quad \text{(equation 13)}$$

This calculation may be performed manually or, as is preferred, by a properly programmed computer. In view of the simple mathematical calculations involved, it is believed unnecessary to describe a suitable computer program in detail as those skilled in the art of automatic data processing and/or in the art of designing CT scanning apparatus will be capable of readily providing a suitable program.

As a check on accuracy, one can compare the lengths of vectors between fixed points as represented in the two different coordinate systems. For example, one can compare vectors A and a. Similarly, one can compare vectors B and b, etc. For improved accuracy, the fiducial plates and hence the measured fiducial points are as far removed from one another as practical. Accuracy on the order of one millimeter in the final calculation of the target frame coordinates can be obtained even though differences of up to 0.35 centimeters are observed between these various vectors with the exemplary illustrated embodiment. Larger differences between vectors A and vectors B, etc., indicates that an error has been made.

In the preferred exemplary embodiment, the fiducial plates are removed from the frame after the cross-sectional slice (FIG. 5) containing the required data has been obtained. Thereafter, the calculated target frame coordinates are utilized for setting up the side bars and probe carrier so as to center the spherical coordinate system of the frame on the target area and permit the desired stereotactic surgery technique to be performed.

It may also be prudent to double check the approximate validity of the calculated target coordinates by performing classical stereotaxis procedures.

While only a few exemplary embodiments have been specifically described in detail above, those skilled in the art will appreciate that many variations and modifications may be made in these exemplary embodiments without materially departing from the novel and advantageous features of this invention. Accordingly, all such variations and modifications are intended to be included within the scope of the appended claims.

What is claimed is:

1. Stereotactic frame apparatus adapted for use in performing stereotactic surgery with an X-ray CT scanner, said stereotactic frame apparatus comprising:
    a stereotactic frame defining a three-dimensional coordinate system which can be fixed with respect to the anatomy of a living patient,
    said stereotactic frame including mechanism for positioning a desired surgical device within said anatomy at any desired location defined in terms of said three-dimensional coordinate system, and
    X-ray detectable fiducial marker means associated with said stereotactic frame defining at least three non-collinear points within each planar cross-section therethrough, said marker means including means for determining the three-dimensional coordinates of said three points in each said cross-section whereby a scan in any single plane provides the three-dimensional coordinates of said three noncollinear points.

2. Apparatus as in claim 1 wherein said X-ray detectable fiducial markers comprise:
    a member having an X-ray detectable feature which intersects any said cross-section at a location which varies depending upon the relative disposition of the cross-section.

3. An improved stereotactic surgery frame of the type defining a three-dimensional coordinate system which can be fixed with respect to the anatomy of a living patient and which can thereafter position a desired surgical device within such anatomy at any desired location defined in terms of said three-dimensional coordinate system, said improvement comprising:
    X-ray detectable fiducial markers physically associated with said frame and defining at least three measurable noncollinear fiducial points, each having predetermined visually determinable three-dimensional coordinates within a single cross-sectional depiction taken through the combination of said anatomy and of said frame and its associated fiducial markers.

4. An improvement as in claim 3 wherein said fiducial markers comprise:
    a plate having a variable cross-section extending a predetermined distance with respect to a first dimension, said predetermined distance varying with respect to a second dimension which is inclined with respect to said first dimension.

5. An improvement as in claim 3 wherein said fiducial markers comprise:
    a member having a detectable feature which intersects any desired cross-sectional depiction at a location which varies depending upon the relative disposition of the cross-section.

6. An improvement as in any one of claim 3-5 wherein said fiducial markers are removably attachable to said stereotactic frame.

7. A method to facilitate stereotactic surgery, said method comprising the steps of:
    fixing a stereotactic surgical frame, having a first predetermined three-dimensional coordinate system, with respect to living tissue,
    scanning the combination of said frame and living tissue with penetrating radiation to provide a cross-sectional depiction thereof in a single plane which includes a desired anatomical target within said living tissue,
    determining the three-dimensional coordinates of said target with respect to a second predetermined three-dimensional coordinate system,
    determining the three-dimensional coordinates of each of at least three non-collinear points located within said cross-sectional depiction in a single plane, both with respect to the three-dimensional coordinate system of said frame and with respect to said second three-dimensional coordinate system, and
    using said determined coordinates to calculate the coordinates of said target with respect to the three-dimensional coordinate system of said frame.

8. A method as in claim 7 wherein said scanning step is performed with an X-ray CT scanner.

9. A method as in claim 7 wherein said fixing step includes the attachment of X-ray detectable fiducial markers to said frame.

10. A method as in claim 7 wherein said second-mentioned determining step includes counting detectable features associated with said frame at predetermined relative locations and present in said cross-sectional depiction.

11. A method as in claim 7 wherein said second-mentioned determining step includes measurement of relative distances between detectable features associated with said frame at predetermined relative locations and present in said cross-sectional depiction.

12. Apparatus for performing three-dimensional stereotactic surgery within the anatomy of a living patient, said apparatus comprising:
    a tomographic scanner having a programmable data processing computer, a CRT display for depicting the relative densities of elemental volumes with a desired planar cross-sectional slice of matter appropriately placed within the CT scanner, and an operator console for entering data and/or instructions into said computer and for identifying the location and relative positional coordinates of any desired element or portion of said slice;
    a rigid frame fixably securable with respect to said anatomy and defining a multi-dimensional coordinate system in which surgical devices can be precisely positioned;
    said frame including plural detectable features which if included as a portion of a single said slice of matter in a single plane, will be represented in said depiction of said cross-sectional slice as a respectively corresponding set of at least three functional points in the plane having predetermined known or readily determinable three-dimensional frame coordinates; and
    said computer being programmed to compute the three-dimensional frame coordinates of any desired anatomical target depicted within said slice as a function of the frame coordinates of said fiducial points and of the relative positional coordinates of said target and said fiducial points within said CRT display.

13. Apparatus as in claim 12 wherein said rigid frame includes at least one detectable feature disposed along a path connecting dissimilar portions of similar spaced-apart frame structures.

14. Apparatus as in claim 12 or 13 wherein said rigid frame includes an inclined rod connected between dissimilar portions of two spaced-apart parallel posts.

15. A method to facilitate stereotactic surgery, said method comprising the steps of:
fixing a stereotactic surgical frame, having a first predetermined multi-dimensional coordinate system, with respect to living tissue,
scanning the combination of said frame and living tissue with penetrating radiation to provide a cross-sectional depiction thereof in a single plane which includes a desired anatomical target within said living tissue,
determining the three-dimensional coordinates of said target with respect to a second predetermined multi-dimensional coordinate system,
determining the three-dimensional coordinates of each of plural points located within said cross-sectional depiction, both with respect to the first multi-dimensional coordinate system of said frame and with respect to said second multi-dimensional coordinate system, and
using said determined three-dimensional coordinates to calculate the three-dimensional coordinates of said target with respect to the multi-dimensional coordinate system of said frame.

16. A method as in claim 15 wherein said scanning step is performed with an x-ray CT scanner.

17. A method as in claim 15 wherein said fixing step includes the attachment of x-ray detectable fiducial markers to said frame.

18. A method as in claim 15 wherein said determining step includes counting detectable features associates with said frame at predetermined relative locations and present in said cross-sectional depiction.

19. A method as in claim 15 wherein said determining step includes measurement of relative distances between detectable features associated with said frame at predetermined relative location and present in said cross-sectional depiction.

20. An improved stereotactic surgery frame of the type defining a multi-dimensional coordinate system which can be fixed with respect to the anatomy of a living patient and which can thereafter position a desired surgical device within such anatomy at any desired location defined in terms of said multi-dimensional coordinate system, said improvement comprising:
fiducial markers physically associated with said frame and defining at least three unique non-collinear measurable fiducial points having determinable three-dimensional coordinates with respect to said frame with a single planar cross-sectional depiction taken through the combination of said anatomy and of said frame and its associated fiducial markers.

21. Apparatus for use in performing stereotactic surgery, said apparatus comprising:
an X-ray CT scanner capable of measuring relative X-ray absorption within elemental volumes of a desired planar cross-section of the anatomy of a living patient and which CT scanner also defines a first multi-dimensional CT scanner coordinate system relative to its own geometrical structure for locating specific anatomical positions with said planar cross-section relative to said first coordinate system,
a stereotactic frame defining a second multi-dimensional coordinate system which can be fixed with respect to the anatomy of a living patient,
said stereotactic frame including mechanism for positioning a desired surgical device within said anatomy at any desired location defined in terms of said second multi-dimensional coordinate system, and
X-ray detectable fiducial markers associated with said stereotactic frame defining plural points within each of said planar cross-sections, each point having determinable coordinates in both said first and said second coordinate systems
said CT scanner including means for transforming the measured CT scan coordinates in three dimensions of a desired portion of the anatomy to corresponding three-dimensional coordinates in said second coordinate system thereby facilitating the use of said stereotactic frame during stereotactic surgery.

22. An improved stereotactic surgery frame of the type defining a three-dimensional coordinate system which can be fixed with respect to the anatomy of a living patient and which can thereafter position a desired surgical device within such anatomy at any desired location defined in terms of said three-dimensional coordinate system, said improvement comprising:
fiducial markers physically associated with said frame and defining at least three measurable non-collinear fiducial points within a cross-sectional depiction taken through the combination of said anatomy and of said frame and its associated fiducial markers.
said fiducial markers including a plate having a variable cross-section extending a predetermined distance with respect to a first dimension, said predetermined distance varying with respect to a second dimension which is inclined with respect to said first dimension, and
said plate having a series of parallel elongated structures with different respective lengths.

23. An improved stereotactic surgery frame of the type defining a three-dimensional coordinate system which can be fixed with respect to the anatomy of a living patient and which can thereafter position a desired surgical device within such anatomy at any desired location defined in terms of said three-dimensional coordinate system, said improvement comprising:
fiducial markers physically associated with said frame and defining at least three measurable non-collinear fiducial points within a cross-sectional depiction in a plane taken through the combination of said anatomy and of said frame and its associated fiducial markers,
said fiducial markers including a member having an X-ray detectable feature which intersects any desired cross-sectional depiction at a location which varies depending upon the relative disposition of the cross-section, and
said member comprising a plate having a series of parallel elongated structures with different respective lengths.

24. An improvement as in claim 22 or 23 wherein said parallel elongated structures are regularly spaced and of substantially equal dimensions and wherein said respective lengths progressively increase or decrease from one structure to the next.

25. An improvement as in any of claims 22 or 23 comprising a plurality of said plates each being adapted for physical attachment to a respectively corresponding portion of said stereotactic frame.

26. Apparatus for performing three-dimensional stereotactic surgery within the anatomy of a living patient, said apparatus comprising:

a tomographic scanner having a programmable data processing computer, a CRT display for depicting of the relative densities of elemental volumes within a desired planar cross-sectional slice of matter appropriately placed with the CT scanner, and an operator console for entering data and instructions into said computer and for identifying the location and relative positional coordinates of any desired element or portion of said slice;

a rigid frame fixably securable with respect to said anatomy and defining a multi-dimensional coordinate system in which surgical devices can be precisely positioned;

said frame including plural detectable features which, if included as a portion of said matter, will be represented in said depiction of said planar cross-sectional slice as respectively corresponding plural fiducial points having predetermined known or readily determinable frame coordinates; and said computer being programmed to compute the frame coordinates of any desired anatomical target depicted within said slice as a function of the frame coordinates of said fiducial points and of the relative positional coordinates of said target and said fiducial points with said CRT display, said rigid frame including three fiducial plates, each having a plurality of parallel elongated structures of varying length.

27. Stereotactic frame apparatus adapted for use in performing stereotactic surgery, said apparatus comprising:

an X-ray CT scanner means capable of measuring relative X-ray absorption within elemental volumes of a desired cross-section of the anatomy of a living patient and which CT scanner means defines a first three-dimensional CT scanner coordinate system relative to its own geometrical structure for locating specific anatomical positions within said cross-section relative to said first coordinate system, a stereotactic frame defining a second three-dimensional coordinate system which can be fixed with respect to the anatomy of a living patient, said stereotactic frame including mechanism for positioning a desired surgical device within said anatomy at any desired location defined in terms of said second three-dimensional coordinate system, and X-ray detectable fiducial markers associated with said stereotactic frame defining at least three noncollinear points within each of said cross-sections, each point having determinable coordinates in both said first and said second coordinate systems such that the measured CT scan coordinates of a desired portion of the anatomy can be transformed to corresponding coordinates in said second coordinate system thereby facilitating the use of said stereotactic frame during stereotactic surgery, each of said X-ray detectable fiducial markers comprising a member having a series of parallel elongated structures therein with different respective lengths and interacting any said cross-section at a location which varies depending upon the relative disposition of the cross-section.

28. Apparatus as in claim 27 wherein said parallel elongated structures are regularly spaced and of substantially equal dimensions and wherein said respective lengths progressively increase or decrease from one slot to the next.

29. Apparatus as in claim 27 or 28 comprising a plurality of said members each being adapted for physical attachment to a respectively corresponding portion of said stereotactic frame.

30. Apparatus as in claim 27 or 28 wherein said X-ray detectable fiducial markers are removably attachable to said stereotactic frame.

31. Stereotactic frame apparatus adapted for use in performing stereotactic surgery, said apparatus comprising an X-ray CT scanner means capable of measuring relative X-ray absorption within elemental volumes of a desired cross-section of the anatomy of a living patient and which CT scanner means defines a first three-dimensional CT scanner coordinate system relative to its own geometrical structure for locating specific anatomical positions within said cross-section relative to said first coordinate system, a stereotactic frame defining a second three-dimensional coordinate system which can be fixed with respect to the anatomy of a living patient, said stereotactic frame including mechanism for positioning a desired surgical device within said anatomy at any desired location defined in terms of said second three-dimensional coordinate system, X-ray detectable fiducial markers associated with said stereotactic frame defining at least three noncollinear points within each of said cross-sections, each point having determinable coordinates in both said first and said second coordinate systems such that the measured CT scan coordinates of a desired portion of the anatomy can be transformed to corresponding coordinates in said second coordinate system thereby facilitating the use of said stereotactic frame during stereotactic surgery, said frame including spaced-apart posts; and said markers including a rod extending between dissimilar portions of pairs of said spaced-apart posts.

* * * * *